United States Patent [19]

Rodero

[11] Patent Number: 4,923,698
[45] Date of Patent: May 8, 1990

[54] BIOACTIVE FILM-FORMING COMPOSITION FOR CONTROL OF CRAWLING INSECTS AND THE LIKE

[75] Inventor: Alejandro Rodero, Racine, Wis.

[73] Assignee: S. C. Johnson & Son, Inc., Racine, Wis.

[21] Appl. No.: 294,328

[22] Filed: Jan. 6, 1989

Related U.S. Application Data

[62] Division of Ser. No. 943,405, Dec. 19, 1986, Pat. No. 4,822,614.

[51] Int. Cl.$^5$ .................. A01N 25/00; A01N 25/34; A01N 25/02; A61L 9/04
[52] U.S. Cl. .................. 424/405; 424/409; 424/DIG. 10; 424/43; 424/45; 514/918; 514/919; 514/939; 514/531; 514/938; 514/521; 514/718; 514/731
[58] Field of Search .................. 424/405, 408, 409; 8/DIG. 10, 43, 45; 514/918, 919, 939, 531, 938, 521, 718, 731

[56] References Cited

U.S. PATENT DOCUMENTS

| | | | |
|---|---|---|---|
| 3,303,091 | 2/1967 | Marlander et al. | 424/45 |
| 4,439,342 | 3/1984 | Albanese | 424/43 |

FOREIGN PATENT DOCUMENTS

| | | | |
|---|---|---|---|
| 2109236 | 6/1983 | United Kingdom | 424/45 |

*Primary Examiner*—Joseph L. Schofer
*Assistant Examiner*—Carmen Pili-Curtis

[57] ABSTRACT

A film-forming bioactive composition for control of crawling insects and the like is disclosed. Also disclosed are methods of producing and utilizing the bioactive composition. The bioactive composition comprises a water-in-oil emulsion, a bioactive ingredient dispersed throughout the emulsion, and a lubricating agent also dispersed throughout the emulsion. The water-in-oil emulsion comprises a continuous phase, an aqueous discontinuous phase, and an emulsifier system for dispersing the discontinuous phase throughout the continuous phase. The bioactive composition of the present invention is characterized in that after particles of the instant bioactive composition have been applied to a surface, a substantial portion of the continuous and discontinuous phases will evaporate over time, leaving a residual film on the surface. Such film comprises the emulsifier system, the bioactive ingredient, and the lubricating agent. The film not only effectively and substantially adheres to the surface for an extended period of time while retaining a high degree of residuality, but the surface-applied bioactive ingredient-containing residue is itself sufficiently slippery to pests such as crawling insects and the like, thereby providing a substantial and effective positive barrier for controlling crawling pests of this type.

3 Claims, No Drawings

BIOACTIVE FILM-FORMING COMPOSITION FOR CONTROL OF CRAWLING INSECTS AND THE LIKE

REFERENCE TO RELATED APPLICATION

This application is a divisional application of patent application Ser. No. 943,405 filed December 19, 1986, now U.S. Pat. No. 4,822,614 the benefit of which is now claimed for purposes of priority pursuant to 35 U.S.C. §120.

FIELD OF THE INVENTION

This invention is directed to a bioactive film-forming composition, for control of crawling insects such as cockroaches, sewer flies and crickets, and other crawling arthropods such as arachnids. More particularly, the present invention is directed to such a bioactive film-forming composition, which is a liquid and generally adapted to adhere to a surface, for providing an effective barrier against crawling insects and the like.

BACKGROUND OF THE INVENTION

It is well-recognized, in the crawling-insect control art, that one common means of access of crawling insects and the like into a dwelling or office building is via openings such as open sewer pipes, drain lines such as from showers, bath tubs and sinks, and the like.

Use of aerosol insecticidal compositions, for insect-control purposes, is well known. For example, British Pat. No. 1,107,140 (to Mitchell et al.) discloses an aerosol-dispensed, insecticidally-active composition which is applied as a spray. Specifically, Mitchell et al. teach producing a mist that is formulated to remain air-borne for a desired period of time. In the art, such a mist-type aerosol insecticide is referred to as a "flying insect killer" or FIK-type insecticide. In contradistinction, the instant bioactive composition, when dispensed as an aerosol, is formulated to be applied onto a surface, and further, is specifically formulated to adhere effectively and substantially to that surface.

Use of repellent compositions, for insect-control purposes, is also well known. For example, Japanese Pat. Document No. 141375 (to Mikasa) teaches such compositions. In particular, the Mikasa disclosure teaches an aerosol-dispensible composition that is used for repelling a wide variety of organisms, including insects. Still more particularly, the Mikasa composition is disclosed as comprising an original tacky solution. In contradistinction, the bioactive composition of the present invention is generally not tacky to the touch, but rather is slippery.

Throughout my patent application, certain terms will be defined and otherwise utilized for purposes of conciseness, and for purposes of elucidating the features and advantages of the present invention. One of these terms is defined hereinbelow.

The term "residuality" as used herein, in reference to a bioactive composition, means to leave an active ingredient-containing residue such as a film on a surface. Typically, the residue includes, in addition to the active ingredient, a number of other ingredients. In the broad sense, the term "residuality" as used herein relates to the residue, including the active ingredient, that is left on the surface, and which is able to maintain its activity for extended periods of time, i.e. up to six weeks and even more, even though there is a breakdown or decomposition of the residue, including the active ingredient, over time due to exposure to sunlight and the like.

Many conventional bioactive compositions, such as those known in the art as "crawling insect killers" (or CIK-type insecticides), whether solvent-based or water-based, generally leave (on the surface onto which they are applied) only the bioactive ingredients and very little residue or film (exclusive of the active ingredients), for binding the bioactive ingredient to the surface. One problem that is met, of course, is that very little of the bioactive ingredient remains on the surface for an extended period of time, relative to the total amount of bioactive composition that is utilized. Unfortunately, most bioactive compositions of this type (i.e. CIKs that are formulated to leave a residue) tend to sag, and some even tend to run, when applied to a substantially vertical surface. While a sagging bioactive composition may be visually unacceptable to most consumers, bioactive compositions that run down a sloped surface are not only messy but generally ineffective for intended purposes as well.

Accordingly, bioactive compositions that effectively adhere to a surface for extended periods of time, while retaining a high degree of residuality, are currently in demand. Surprisingly, I have discovered a bioactive composition that not only substantially and effectively adheres to a surface for an extended period of time while retaining a high degree of residuality, but the surface-applied bioactive ingredient-containing residue is itself sufficiently slippery to crawling insects and the like as to provide a positive barrier for control of these crawling pests.

SUMMARY OF THE INVENTION

The present invention is directed to a bioactive film-forming composition for control of pests such as crawling insects and the like.

The bioactive composition of the present invention comprises a water-in-oil emulsion, a bioactive ingredient dispersed throughout the emulsion, and a lubricating agent also dispersed throughout the emulsion.

The water-in-oil emulsion comprises a continuous phase, an aqueous discontinuous phase, and an emulsifier system for dispersing the discontinuous phase throughout the continuous phase.

The bioactive composition of the present invention is characterized in that after particles of the instant bioactive composition have been applied to a surface, a substantial portion of the continuous and discontinuous phases will evaporate over time, leaving a residual film on the surface. Such film comprises the emulsifier system, the bioactive ingredient, and the lubricating agent. The film not only effectively and substantially adheres to the surface for an extended period of time while retaining a high degree of residuality, but the surface-applied bioactive ingredient-containing residue is itself sufficiently slippery to pests such as crawling insects and the like, thereby providing a substantial and effective positive barrier for controlling crawling pest of this type.

The bioactive composition may further preferably include additional, optional ingredients if desired.

Illustrative methods of producing and utilizing the bioactive film-forming composition of my present invention are presented hereinbelow.

DETAILED DESCRIPTION OF PREFERRED EMBODIMENTS

While the present invention is susceptible to embodiment in various forms, it is to be understood that the below-presented examples embodying some of the principles of the present invention are merely illustrative and are not to be intended as limiting the scope of my invention.

As I briefly mentioned above, certain terms will be defined and otherwise utilized for purposes of conciseness, and to otherwise elucidate the features and advantages of the present invention.

The term "bioactive composition" as used herein means a composition which includes a "bioactive ingredient", wherein the bioactive ingredient can be an insecticidally-active ingredient, an insect-repellent ingredient, or both. Also, because it is known that certain compounds function not only as toxicants but also as repellents—for certain insects and other arthropods—it is further contemplated that the bioactive ingredient of the present invention may, at times, exhibit dual activity of this sort.

The term "crawling insect" as used herein is defined in a broad sense and includes—in addition to insects—other crawling arthropods such as arachnids as well.

The bioactive film-forming composition of the present invention controls crawling insects and the like by providing a substantial and effective positive barrier.

As briefly mentioned above, the bioactive composition of the present invention comprises a water-in-oil emulsion, a bioactive ingredient dispersed throughout the emulsion, and a lubricating agent also dispersed throughout the emulsion.

The water-in-oil emulsion (sometimes referred to as an "oil-out" emulsion in the art) is present in the bioactive composition in an amount of about 60 to about 99.9 wt.-%, preferably about 80 to about 99 wt.-%, and more preferably about 90 to about 99 wt.-%, based upon the weight of the bioactive composition.

The bioactive ingredient is present in an amount effective to kill and/or repel crawling insects. For example, the bioactive ingredient is generally present in the bioactive composition in an amount of about 0.01 to about 5 wt.-%, preferably about 0.05 to about 2 wt.-%, and more preferably about 0.1 to about 1 wt.-%, based upon the weight of the bioactive composition.

The lubricating agent is present in the bioactive composition in an amount of about 0.1 to about 40 wt.-%, preferably about 1 to about 20 wt.-%, and more preferably about 1 to about 5 wt.-%, based upon the weight of the bioactive composition.

As mentioned above, the water-in-oil emulsion comprises a continuous phase, an aqueous discontinuous phase, and an emulsifier system for dispersing the discontinuous phase throughout the continuous phase.

Based upon the weight of the bioactive composition, the continuous phase is present in an amount of about 2 to about 40 wt.-%, preferably about 4 to about 20 wt.-%, and more preferably about 5 to about 15 wt.-%.

The aqueous, discontinuous phase comprises water.

The aqueous, discontinuous phase is present in an amount of about 55 to about 98 wt.-%, preferably about 70 to about 95 wt.-%, and more preferably about 80 to about 90 wt.-%, based upon the weight of the bioactive composition.

The emulsifier system is present, in the bioactive composition, in an amount of about 0.1 to about 5 wt.-%, preferably about 0.2 to about 2 wt.-%, and more preferably about 0.5 to about 2 wt.-%, based upon the weight of the bioactive composition.

The bioactive composition of the present invention is further characterized as leaving a surface-applied, bioactive ingredient-containing residual film that is substantially water resistant. One method of applying the water-resistant residual film to such a surface is briefly described as follows.

After particles of the above-described, substantially evaporable bioactive composition have been applied to the surface, a substantial portion of the continuous and discontinuous phases will eventually evaporate over time, leaving on the surface a residual, substantially water-resistant film. As mentioned above, the surface-adhering residual film comprises the emulsifier system, the bioactive ingredient, and the lubricating agent. Such film not only substantially and effectively adheres to the surface for an extended period of time while retaining a relatively high degree of residuality, but the surface-applied bioactive ingredient-containing residue is itself sufficiently slippery to most crawling pests, such as insects and the like, as to provide a substantial and effective positive barrier for controlably preventing these crawling pests from entering a home or office building.

One feature of the bioactive film-forming composition of the present invention is the relatively slippery, surface-adhering crawling insect barrier mentioned above. Further in accordance with the principles of the present invention, it can be appreciated that the "slippery"-quality feature of the present invention can be altered as desired.

For example, in some applications, it is desirable that the residual film present a relatively extremely slippery surface to crawling insects and the like. Accordingly, by selecting a suitable lubricating agent, I have not only observed that selected formulations of my bioactive composition effectively adhere to a substantially vertical surface without sagging or running down the surface, but I have further observed that the surface-adhering, substantially water-resistant residual film that remains on the substantially vertical surface after most of the continuous and discontinous phases have evaporated is so slippery that virtually no crawling insect was able to cross it.

Another feature of the present invention is the "lasting" effect of the residual film. That is, by selecting suitable bioactive composition ingredients, the substantially water-resistant residual film can effectively adhere to a surface for extended periods of time, such as 6 weeks and even more, while substantially retaining its bioactive character over this period of time.

While it can be appreciated that some toxicants have repellent qualities (as least toward selected species of insects and other arthropods) it can also be appreciated that many repellents are not toxic to most crawling insects and the like.

Accordingly (and as mentioned above), the bioactive ingredient of the present invention can be a toxicant, can be a repellent, or can be a mixture comprising a toxicant and a repellent.

It can further be appreciated, in view of the "slipperiness" quality of the present invention, that the "physical barrier" aspect of the present composition, even without inclusion of the bioactive ingredient, can be an effective and substantial positive barrier for controling entry by crawling insects and the like into a home or office building via openings (as mentioned above).

Yet in other applications, it is desirable that the residual film be somewhat slippery but generally traverseable by crawling insects. For example, in one such application it may be desirable for a consumer to "see" the remains of a dead insect (to achieve a psychological or other effect). That is, the slipperiness quality of the residual film can be adjusted, by e.g. reducing the relative amount of lubricating agent, by selecting a suitable lubricating agent to achieve the desired, less-slippery effect, or the bioactive composition itself can be reformulated to include suitable, optional ingredients such as waxes, powders and the like which would tend to achieve the desired, less-slippery effect, while retaining in the reformulated bioactive composition an effective amount of the insecticidally-active ingredient, so that the band of residual film (of predetermined width) that forms on the surface has a desired time for killing contact.

While in still other applications, it is desirable that the residual film volatilize over time; and it can be appreciated that the present composition can include a suitable, volatilizable lubricating agent so that the residual film will volatilize over time, as desired.

The bioactive film-forming composition of the present invention has a viscosity effective to enable particles (of the bioactive composition) to substantially and effectively adhere to a surface. The bioactive composition accordingly has a viscosity of about 50 to about 30,000 centistokes, preferably about 500 to about 10,000 centistokes, and more preferably about 2,000 to about 8,000 centistokes.

As mentioned above, the water-in-oil emulsion comprises a continuous phase, an aqueous discontinuous phase, and an emulsifier system for dispersing the discontinuous phase throughout the continuous phase.

The continuous phase comprises a nonaqueous hydrocarbon-based solvent.

Illustrative of suitable hydrocarbon solvents useful in accordance with the present invention are those having boiling ranges of about 80° to about 200° C. and preferably having boiling ranges of about 95° to about 150° C. Isoparaffinic hydrocarbon solvents such as those commercially available from Exxon Corporation under the brand name "Isopar", are especially suitable.

A presently preferred solvent is selected from the group consisting of kerosene, mineral spirits, isoparaffinic hydrocarbons, and the like.

For any one of the above-mentioned solvents, the relative amount of solvent that is present in the bioactive composition, can be varied to make the bioactive composition more viscous or less viscous, as desired. Generally, decreasing the amount of solvent relative to the aqueous discontinuous phase, with emulsification, causes the resultant emulsion to become more paste-like; and increasing the amount of solvent relative to the aqueous discontinuous phase, with emulsification, tends to lower the viscosity of the resultant emulsion. Too low of a viscosity may cause the bioactive composition to run or sag, which is (as indicated above) undesirable.

As briefly mentioned above, a suitable bioactive ingredient, in accordance with the principles of the present invention, might exhibit insecticidally-active characteristics, might exhibit or possess insect-repellent characteristics, or might exhibit some degree of both.

A suitable bioactive ingredient must be capable of being dispersed throughout the continuous phase. Certain suitable bioactive ingredients are relatively soluble in the continuous phase.

Illustrative of the insecticidally-active ingredients that are suitable, for purposes of the present invention, include cypermethrin, other synthetic pyrethroids (such as permethrin, deltamethrin, alphamethrin, and cyphenothrin and the like), natural pyrethrum, organo phosphates, and the like. One such suitable organo phosphate is known in the art by its brand name "Dursban" (i.e. chlorpyrifos).

A presently preferred insecticidally-active ingredient is selected from the group consisting of cypermethrin and permethrin.

Suitable insect-repellent ingredients include certain synthetic pyrethroids (i.e. such as those having intrinsic repellancy), N,N-diethyl-meta-toluamide (usually referred to as "Deet" in the art), BHA and BHT (see, e.g., *Nutrition and Food*, Vol. 14, pages 378–383, by Kajimoto et al., published 1962), and Botanicals such as Neem extract (see, e.g., "Natural Pesticides from the Neem Tree", Proceedings of the First International Neem Conference, Rottach-Egern, Federal Republic of Germany, 16–18 June, 1980, by H. Schmutterer, K.R.S. Ascher, and H. Rembold), Sembury extract, and the like. (Although, for some emulsions, it may be desirable to utilize relatively low levels of Deet in order to avoid well-known, undersirable effects.)

As mentioned above, the emulsifier system is utilized to disperse the aqueous, discontinuous phase throughout the continuous phase.

Suitable emulsifier systems, in accordance with the present invention, are selected from the group consisting of a liquid, nonionic sorbitan monooleate having an HLB value of about 4.3 (such as that having the brand name "Span 80"), a mixture comprising the above-mentioned liquid, nonionic sorbitan monooleate having an HLB value of about 4.3 (e.g. "Span 80") and a liquid, nonionic sorbitan monooleate polysorbate having an HLB value of about 15 (such as that having the brand name "Tween 80"), a mixture comprising the above-mentioned liquid, nonionic sorbitan monooleate having an HLB value of about 4.3 (e.g. "Span 80") and an ethoxylated fatty acid (such as stearic acid) having about 3.5 moles of ethylene oxide per mole of stearic acid (such as that having the brand name "Ethofat 3.5 MEO"), and the like.

A presently preferred emulsifier system is selected from the group consisting of the mixture comprising Span 80 and Tween 80, and the mixture comprising Span 80 and Ethofat 3.5 MEO.

In the emulsifier system mixture comprising Span 80 and Tween 80, a suitable level of the first ingredient, for purposes of the present invention, is about 85 to about 100 wt.-% Span 80, preferably above 90 to about 100 wt.-% Span 80, and more preferably about 90 to about 95 wt.-% Span 80, with the balance of this emulsifier system mixture being Tween 80, based upon the weight of the emulsifier system mixture.

Whereas in the emulsifier system mixture comprising Span 80 and Ethofat 3.5 MEO, a suitable level of the first ingredient, for purposes of the present invention, is about 20 to about 35 wt.-% Span 80, preferably about 25 to about 30 wt.-% Span 80, and more preferably about 27 wt.-% Span 80, with the balance of this emulsifier system mixture being Ethofat 3.5 MEO, based upon the weight of the emulsifier system mixture.

Suitable lubricating agents, in accordance with the principles of the present invention, include silicones, mineral oils, petrolatum, polybutenes, and the like, and blends of each of these (i.e. each such lubricating agent including a blend of different molecular weights and viscosities of any one of the above-named lubricating-agent types).

Illustrative of the silicones that are suitable for purposes of the present invention are the organic polysiloxanes including polydialkyl siloxane, polyalkylaryl siloxane, and polydiaryl siloxane. Polysiloxanes such as polydimethyl siloxane, polydiethyl siloxane, polymethylethyl siloxane, polymethylphenyl siloxane, and copolymers of two or more of such siloxanes are exemplary of the materials which can be used. Polydimethyl siloxane is especially preferred, particularly combinations of the polydimenthyl siloxanes having different viscosities ranging at from about 5 to about 50,000 centistokes, and preferably at from about 100 to about 10,000 centistokes.

A presently preferred lubricating agent is selected from the group consisting of mineral oil and silicone. An especially preferred silicone is a dimethyl polysiloxane fluid having a viscosity, at room temperature (i.e. about 25° C.), of about 500 centistokes (one such silicone having the brand name "Dow Corning 200 Fluid", commercially available from Dow Corning of Midland, Michigan).

The film-forming bioactive composition of the present invention can be dispensed from various types of dispensing systems and equipment including, but not limited to, spray guns and portable aerosol cans, for providing an advantageous way of applying the bioactive composition of the present invention onto a variety of surfaces such as on surfaces surrounding cracks and crevices, beneath doors and around windows, in pipe and other conduit, for providing the positive barrier mentioned above.

For convenience, the bioactive film-forming composition of the present invention further preferably comprises an effective amount of a propellent, to enable the bioactive film-forming composition of the present invention to be dispersed in an aerosol form so that the present composition can conveniently and effectively be applied to a desired surface.

Suitable propellents for these purposes include, but are not limited to, liquified and compressed gases.

Illustrative of suitable liquified gases, for purposes of the present invention, are hydrocarbon propellents (such as the commercially available $C_1$ to $C_4$ hydrocarbons), and hydrofluorocarbon propellents and other halogenated propellents (such as a variety of commercially available halogenated propellents, known in the art by the brand names "Freon", "Dymel", "Genetron", "Isotron", and the like). Illustrative of the preferred hydrocarbon propellents are propane, n-butane, isobutane, and mixtures thereof. Suitable compressed gases include air, nitrogen, nitrous oxide, and carbon dioxide.

A presently preferred propellent, known in the art as "A-46", has a vapor pressure of about 46 pounds per square inch gauge (psig) and comprises about 80 mole percent isobutane and about 20 mole percent propane.

When the bioactive composition of the present invention comprises (1) the water-in-oil emulsion, (2) the bioactive ingredient, (3) the lubricating agent, and (4) the propellent, the propellent is present in an amount of about 4 to about 50 wt.-%, preferably about 8 to about 30 wt.-%, and more preferably about 15 to about 25 wt.-%, based upon the weight of the bioactive composition as defined herein.

When the bioactive composition includes the propellent, it may be necessary to increase or decrease the relative amounts of solvent and lubricating agent, to maintain a desired viscosity range or value for the bioactive composition.

As briefly mentioned above, the film-forming bioactive composition can advantageously further comprise additional, optional ingredients.

One such optional ingredient, a wax that is known in the art as "Tan Microcrystalline Wax, 165/170" (i.e. a synthetic wax), is utilized to better control the degree by which the present film-forming bioactive composition attaches to a desired surface. In the alternative (or in addition to the above stated purpose), the wax can further be utilized to lessen the probability that the bioactive film-forming composition will sag when applied to the surface. Other suitable wax ingredients of this sort include a synthetic wax ingredient known in the art as "Microwax 150/160", including the synthetic waxes generally referred to as paraffin waxes, and the natural waxes such as beeswax, candelilla and carnauba.

In addition to the above-identified optional ingredients, the bioactive film-forming composition of the present invention can further optionally include a fragrance, a microorganism growth inhibitor or preservative, and-/or a metal-corrosion inhibitor. It can be appreciated that inclusion of a preservative and/or a metal-corrosion inhibitor may be desirable (depending upon the application and/or use), for a variety of reasons. One presently preferred microorganism growth inhibitor or preservative is formaldehyde.

The bioactive film-forming composition of the present invention can still further optionally include a disinfectant agent, a dye or pigment to produce colored films, cleansing agents to clean the surface onto which the film is applied, and the like, if desired.

Additional optional ingredients include perfumes, powdered silicas and other powdered ingredients, and the like.

Further principles of the present invention can be ascertained from the following examples.

EXAMPLE 1

Bioactive Composition, Able To Adhere To A Surface And Produce A Water-Insoluble Film, For Providing A Water-Resistant Insect Barrier

| Ingredient | Function Served | Wt. % |
| --- | --- | --- |
| Kerosene | Solvent utilized to provide the continuous phase | 6.00 |
| Water | Utilized to provide the discontinuous phase | 69.80 |
| Cypermethrin | Bioactive ingredient | 0.30 |
| Span 80 | First ingredient of the emulsifier system | 0.93 |
| Tween 80 | Second ingredient of the emulsifier system | 0.07 |
| Silicone | Lubricating agent | 2.00 |
| Tan Microcrystalline Wax 165/170 | Optional ingredient. Affects the coefficient of friction of a surface, to render the surface more/less slippery and/or more tacky | 0.70 |
| Formaldehyde | Optional ingredient. Growth inhibitor or preservative. | 0.20 |
| "A-46" Propellent | Optional ingredient. Used to produce the desired aerosol droplet or particle size | 20.00 |

EXAMPLE 2

Method Of Producing The Film-Forming Bioactive Composition Of Example 1

The optional synthetic wax ingredient was placed into a suitable container and was heated, at a temperature of about 75° to about 80° C., for melting the wax. Next, the silicone, the cypermethrin, the kerosene, and the emulsifier system ingredients, were added into the container and incorporated into the melted wax, utilizing agitation, thereby producing the continuous phase. The optional formaldehyde ingredient and the water were next combined at room temperature (i.e. about 25° C.), utilizing agitation, in a separate suitable continer, thereby producing the aqueous discontinuous phase. Then the continuous and aqueous discontinuous phases were combined, preferably relatively slowly and utilizing agitation, thereby producing the bioactive film-forming composition of the present invention. Preferably, the aqueous discontinuous phase was poured into the continuous phase. (Typically, a white emulsion, which thickens considerably in viscosity with the addition of the water phase, will be observed to form.) The bioactive composition containing the optional ingredients was then placed together with the propellent in an aerosol container, and the aerosol container sealed and pressurized.

What has been described herein is a novel bioactive film-forming composition for control of crawling insects and the like. While the novel composition including the method of producing the composition have been described with reference to preferred embodiments, the invention is not limited thereto.

For example, the bioactive composition discussed herein is preferably utilized to produce a residual, bioactive, water-resistant film on a surface. Because the residual film is an oil-out emulsion, it readily adheres to most vertical surfaces without sagging. In particular, within 24 hours after the bioactive composition is applied to a surface, most of the volatilizable ingredients (i.e. most of the continuous and discontinuous phases) will have evaporated leaving behind a relatively thin, water-resistant, often semi-transparent film containing the bioactive ingredients. Moreover, because the film-forming and bioactive ingredients that are utilized are water insoluble, the film which adheres to the surface not only contains the bioactive ingredients but also is water resistant (i.e. after the volatilizable components of the bioactive composition evaporate).

Advantageously, the residual film does not build up on drains and pipes because the film that is deposited is normally very thin, so that such a film typically eventually wears away through normal use of the pipes, using water, detergents and the like.

Moreover, such a film can specifically be formulated to be oily and very slippery, for preventing crawling insects from climbing along a substantially vertical surface. Yet the film substantially and effectively adheres to the surface without sagging.

In the event that crawling insects are able to traverse the film-treated surface (i.e. crossing the bioactive film when the film is applied, for example, to a horizontal surface), the presence in the bioactive composition of an effective amount of a suitable insecticidally-active ingredient substantially insures desired "insect kill", if the crawling insect has made contact with the film.

Moreover, a variety of commercially-available emulsifier systems can be utilized to affect the nature of the oil-out emulsion, as desired.

Still further, the relative proportions of the various ingredients, such as silicone, mineral oil, and wax, can readily be altered to increase or decrease the degree of residual film slipperiness and/or the ability of the residual film to adhere to a substantially vertical surface without sagging.

Thus, alternatives, changes or modifications will become apparent to those skilled in the art upon reading the foregoing description. Accordingly, such alternatives, changes and modifications are to be considered as forming a part of my invention insofar as they fall within the spirit and scope of the appended claims.

I claim:

1. A method of applying a substantially evaporable bioactive composition onto a surface, wherein the bioactive composition is characterized as being able to provide a substantial and effective positive barrier for control of crawling insects and the like, the method comprising the steps of:

combining a lubricating agent, a bioactive ingredient, an evaporable solvent, and an effective amount of an emulsifier system, with agitation, for producing a substantially evaporable emulsified continuous phase, wherein the bioactive ingredient is selected from the group consisting of an insecticidally-active ingredient, an insect-repellent ingredient, and combinations thereof, wherein the insecticidally-active ingredient is selected from the group consisting of synthetic pyrethroids, natural pyrethrum, and organo phosphates, and wherein the insect-repellent ingredient is selected from the group consisting of synthetic pyrethroids having intrinsic repellancy, N,N-diethyl-meta-toluamide, BHA, BHT, Neem extract and Sembury extract;

adding water to the continuous phase, utilizing agitation, thereby producing the bioactive composition, wherein the lubricating agent is present in an amount of about 1 to about 20 weight percent based upon the weight of the bioactive composition, wherein the lubricating agent is selected from the group consisting of silicones, mineral oils, petrolatum and polybutenes, and blends of each of these;

applying particles of the bioactive composition onto the surface; and evaporating a substantial portion of the surface-applied bioactive composition, thereby producing a bioactive film on the surface, wherein the bioactive film provides the substantial and effective positive barrier for control of crawling insects.

2. The method in accordance with claim 1 and further comprising, after the water-adding step, containing the bioactive composition in a pressurized container.

3. The method in accordance with claim 2 wherein the pressurized container contains a propellent in an amount effective to cause the bioactive composition to be aerosol-dispersible from the pressurized container, for enabling particles of the aerosol-dispersed bioactive composition to substantially and effectively adhere to the surface.

* * * * *

UNITED STATES PATENT AND TRADEMARK OFFICE
CERTIFICATE OF CORRECTION

PATENT NO. : 4,923,698

DATED : May 8, 1990

INVENTOR(S) : Alejandro Rodero

It is certified that error appears in the above-identified patent and that said Letters Patent is hereby corrected as shown below:

At col. 9, line 14, please delete "continer" and please substitute the word -- container -- in place thereof.

Signed and Sealed this

Third Day of March, 1992

Attest:

HARRY F. MANBECK, JR.

*Attesting Officer*      *Commissioner of Patents and Trademarks*